United States Patent [19]

Carrico, Jr. et al.

[11] Patent Number: 5,419,279
[45] Date of Patent: May 30, 1995

[54] APPARATUS FOR DEPOSITING AND STAINING CYTOLOGICAL MATERIAL ON A MICROSCOPE SLIDE

[75] Inventors: Charles L. Carrico, Jr.; William A. Fox, both of Burlington; Ernest A. Knesel, Jr., Greensboro, all of N.C.

[73] Assignee: Hoffmann-La Roche Inc., Nutley, N.J.

[21] Appl. No.: 218,049

[22] Filed: Mar. 14, 1994

Related U.S. Application Data

[63] Continuation of Ser. No. 953,037, Sep. 29, 1992, abandoned.

[51] Int. Cl.$^6$ .............................................. B05C 3/20
[52] U.S. Cl. ................................... 118/406; 118/407; 118/421; 118/504; 359/391; 359/396
[58] Field of Search ............. 118/400, 406, 407, 421, 118/504; 269/294; 359/391, 396, 398, 819, 827, 828, 894

[56] References Cited

U.S. PATENT DOCUMENTS

| | | | |
|---|---|---|---|
| 2,643,581 | 6/1953 | Wehrenfennig | 359/828 X |
| 3,904,781 | 9/1975 | Henry | 359/398 X |
| 4,659,179 | 4/1987 | Dominique et al. | 359/396 |
| 4,688,513 | 8/1987 | Eberle | 118/52 |
| 4,697,543 | 10/1987 | Abbott et al. | 118/421 X |
| 4,946,266 | 8/1990 | Kraft et al. | 359/391 |

FOREIGN PATENT DOCUMENTS 201780 4/1986 European Pat. Off. .
9104438 4/1991 Germany .

OTHER PUBLICATIONS

Derwent Abstract No. 86-306585 which corresponds to EP 201 780.
Lehmitz, Reinhard., *Medizintechnik*, vol. 28, No. 3, pp. 86–87 (1988)–Zuerich CH, XP122740.

*Primary Examiner*—Michael W. Ball
*Assistant Examiner*—Francis J. Lorin
*Attorney, Agent, or Firm*—George M. Gould; George W. Johnston; John P. Parise

[57] ABSTRACT

An apparatus for use in depositing and staining cytological material on a microscope slide has an elongated hollow tube, a base member, at least one flange, and a base plate. The base member is attached to the bottom end of the tube and projects outwardly from the tube perpendicular to the longitudinal axis of the tube. At least one flange is connected to the base member and outwardly-extends from the base member perpendicular to the longitudinal axis of the tube. The base member has a recessed area configured to receive the microscope slide, and slots configured and dimensioned to receive the flange. A passage in the base plate extends from each slot to releasably secure the respective flange when the tube is rotated. As designed, this apparatus advantageously allows individual staining of a slide, thereby preventing false-positive results due to floater cells which can translocate between slides in a common bath.

4 Claims, 3 Drawing Sheets

APPARATUS FOR DEPOSITING AND STAINING CYTOLOGICAL MATERIAL ON A MICROSCOPE SLIDE

This is a continuation of application Ser. No. 07/953,037, filed Sep. 29, 1992, now abandoned.

FIELD OF THE INVENTION

The invention pertains to an apparatus for depositing and staining cytological material on a microscope slide.

BACKGROUND OF THE INVENTION

Standard cell preparations for cytological evaluation have, in the past, been produced by spreading or smearing a swab collection of cells across a microscope slide surface and allowing the cells to dry. This procedure often produces a preparation that contains unreadable areas of cells due to contaminates, distorted morphology, folding of the cells, and the overlapping of the cells.

Other methods of depositing cell onto microscope slides include centrifugation of cells onto slide, and hematology smearing.

An attempt to overcome the above described difficulties was made with the apparatus described in U.S. Pat. No. 4,688,513 to Eberle. In general, Eberle teaches a centrifugal chamber for coating slides with a sedimentation product. The apparatus includes a cylindrical sample chamber with a microscope slide abutting one end of the sample chamber. The microscope slide is mounted on a flat surface of a carrier plate which carrier plate is removably connected with the chamber-microscope slide assembly. The mechanism for locking the chamber to the carrier plate is a linearly-displaceable locking slide which is permanently attached to the carrier plate. Alternately, the chamber can be connected to the carrier plate via rotatable disk-like locking mechanism which also is permanently attached to the carrier plate. The sample fluid containing the cells to be analyzed is placed in the chamber and the apparatus then is placed in a centrifuge. After centifuging, the supernatant is removed and then the cylindrical chamber is removed from the assembly. The microscope slide, with the centifuged cells adhered thereto, is removed and the cells then are stained using conventional methodology.

A main disadvantage of the apparatus according to the Eberle patent is that it produces cell collections which contain overlapping cells, cells which have folded over onto themselves during centrifugation, and cells which have a distorted morphology as a result of the centrifugal force.

Another disadvantage of the Eberle device is that the slides must be removed from the assembly in order for the cells to be stained using standard staining methods. With standard Pap-staining techniques, a plurality of the prepared slides containing the cell collections are all immersed into a vessel containing the stain solution. Because slides from different patients are usually near one another in the stain solution, there is a risk that some cells from one patient's slide may become dislodged and float over to and adhere to a different patient's slide. Such "floaters" can generate false-positive results if the floater cell is abnormal and adhere's to a slide containing only normal cells. To overcome the obvious disadvantages of such a procedure, it is important to ensure that the cell collections are isolated from other specimen slides.

SUMMARY OF THE INVENTION

The invention pertains to an apparatus for depositing and staining cytological material on a microscope slide. The apparatus includes an elongated hollow tube having with a top end and a bottom end and having a base member which extends outwardly from and perpendicular to the longitudinal axis of the tube. The base having at least one outwardly-extending connector flange. The outwardly-extending connector flange has a guide flange positioned at the terminal end thereof, which guide flange is disposed substantially perpendicular to the outwardly-extending connector flange. The apparatus also includes a base plate which defines a recess configured for receiving a microscope slide. The base plate also includes slots configured and dimensioned to receive and releasably secure the outwardly-extending connector flange of the hollow tube. When the outwardly-extending flange is releasably secure in the slot of the base plate, the elongated hollow tube is positioned to fastenably hold the microscope slide which is securely confined to the recessed area of the base plate.

DETAILED DESCRIPTION OF THE INVENTION

Figure 1:
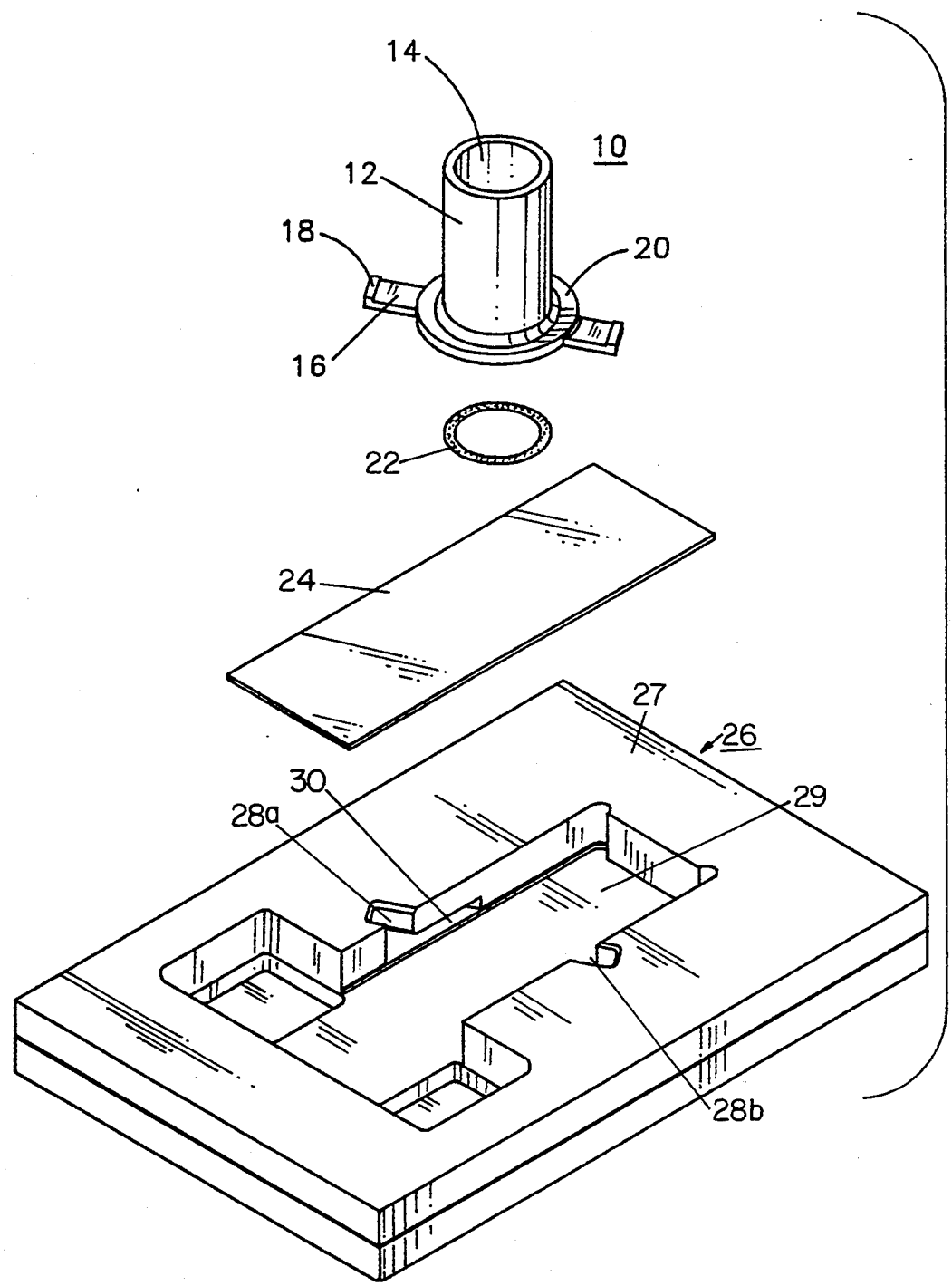
FIG. 1 is an exploded view of an embodiment of the elongated hollow tube, microscope slide, and base plate assembly of the invention.
Figure 2:
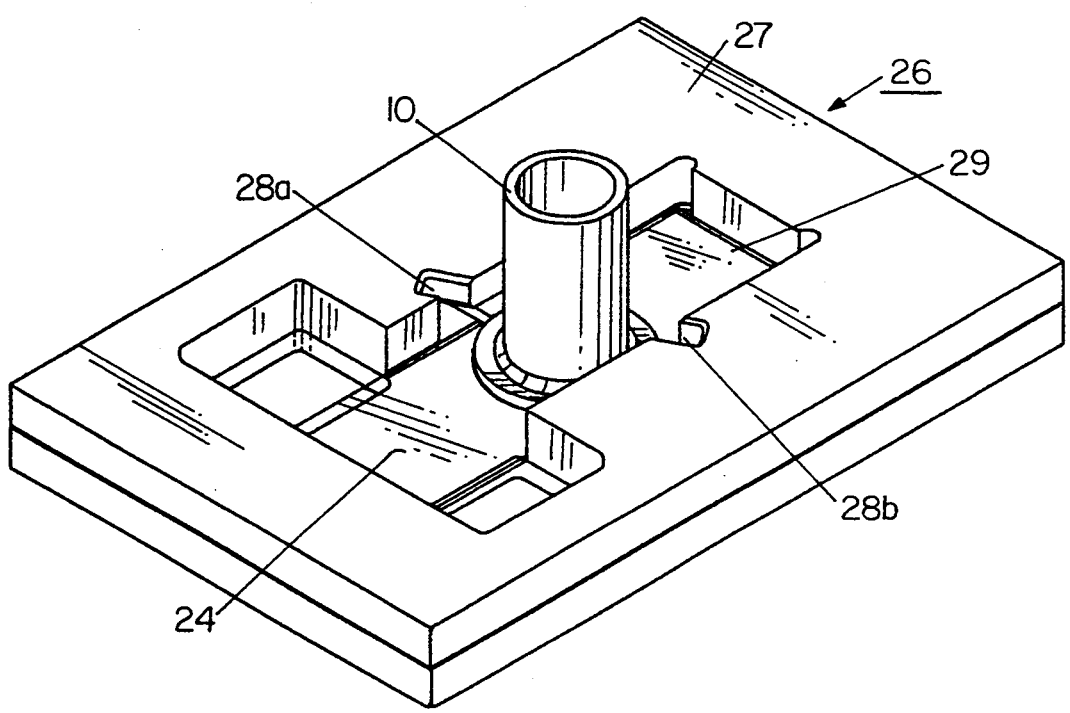
FIG. 2 is a perspective view of an embodiment of the invention when fully assembled.
Figure 3:
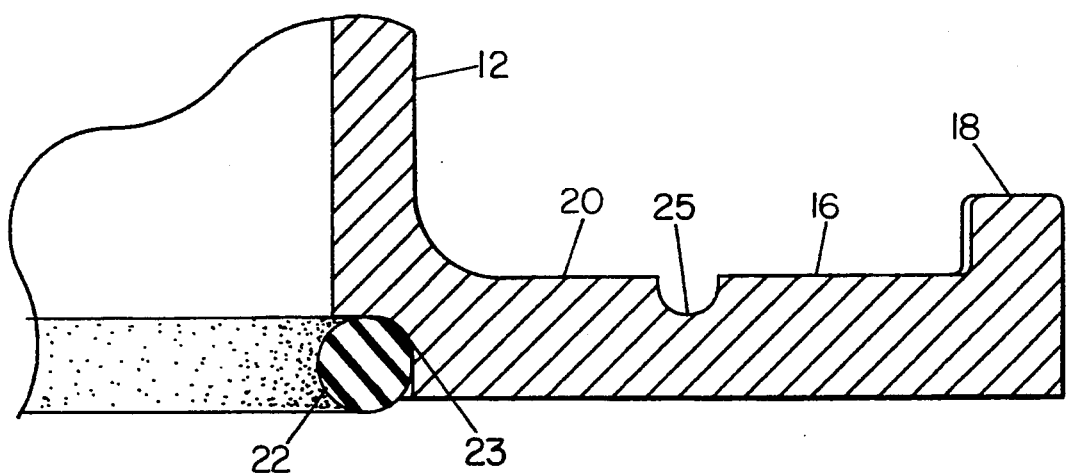
FIG. 3 is a partial cross-sectional view of the elongated hollow tube and O-ring assembly.

The invention is directed to an apparatus for depositing and staining cytological material on a microscope slide. Referring to FIGS. 1 and 2, of a preferred embodiment of the invention is shown. Reference numeral 12 indicates a side wall of the elongated hollow tube 10, which side wall 12 defines an inner chamber 14. The exact dimensions of the inner diameter of the tube 10 is not critical to the invention. However, it is important that the inner diameter of the tube 10 be less than the width of the microscope slide onto which is to be placed. The tube 10 also includes, in a preferred embodiment, a pair of outwardly-extending connector flanges 16 which are integrally formed with a base member 20 which is disposed at the bottom end of the side wall 12. Preferably, the base member 20 is disk-shaped as shown in the Figures, however, it can be of any shape. It is apparent that one or more connector flanges 16 can be suitable for use in the apparatus of the invention. The base member 20 is an aspect of a preferred embodiment of the invention as it assists in providing structural support to the tube 10. It is apparent that a disk-shaped, or any other shaped base, is not necessary for the practice of the apparatus of the invention. As shown in FIG. 1, the base member 20 has a diameter greater than the diameter of the cylindrical side wall 12. FIG. 1 also shows that the outwardly-extending connector flanges 16 are each provided with a guide flange 18 positioned at the terminal end of the flange 16. Each guide flange 18 is substantially perpendicularly disposed to the connector flange 16, thus forming a shape resembling the letter "L". FIG. 2 shows a sealing member 22, which in a preferred embodiment, is an O-ring or similar device, disposed at the bottom end of the tube 10 where the tube abuts the surface of the microscope slide. As shown in FIG. 3, an annular groove 23 is defined by the side wall 12 and the base member 20 for removably and securely receiving the O-ring 22.

The base plate 26, as shown in FIG. 1, comprises a recessed area 29 which receives and confines a microscope slide 24. The recessed area 29, in a preferred embodiment, is configured and dimensioned to conform to the shape of a microscope slide such that when a slide is placed on the flat surface in the recessed are 29, it is prevented from substantial side-to-side or end-to-end movement. This facilitates cell deposition and staining on a series of slides which have cell collections located in approximately the same location on the slides, which then promotes the use of the slides on automated slide analyzing equipment. The base plate 26 also includes slots 28a. 28b which extend outwardly from the recessed area 29 and which slots 28a, 28b receive the outwardly-extending connector flanges 16. Formed within each slot 28a, 28b is a passage 30 which is preferably formed substantially parallel to the flat surface of recessed area 29. Each slot 28a, 28b and passage 30 is configured and dimensioned to receive and releasably securely hold a connector flange 16, and a guide flange 18 when the tube 10 is rotated.

It will be apparent that the tube 10 can be manufactured from any type of material, however, it is preferred that the tube 10 be manufactured from polyethylene or other similar material. The base 26 can be made of any rigid durable material. However, it is preferred that the base plate 26 be formed of aluminum or steel, or other similar material.

FIG. 3 is a partial cross-sectional view of the elongated tube 10, showing the side wall 12 of tube 10, base member 20, connector flange 16, and guide flange 18. Also depicted is an annular grove 23 which receives and securely holds the O-ring 22 in place. In a preferred embodiment, notch 25 is defined in connector flange 16 to provide added flexibility to the connector flange 16.

Figure 4:
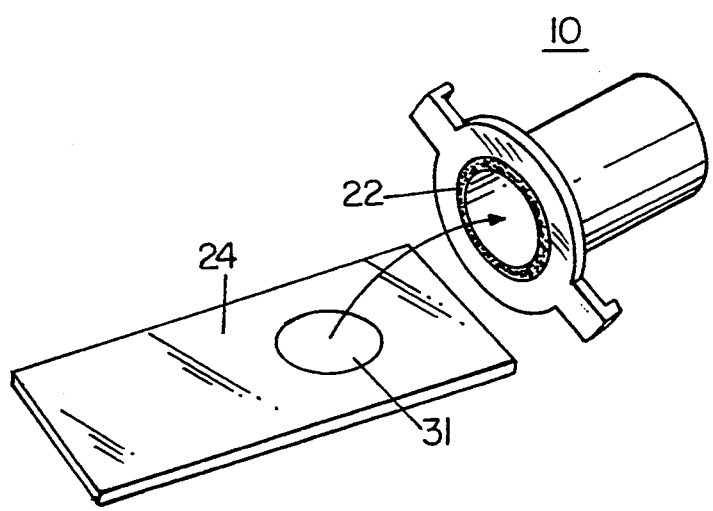
FIG. 4 is a perspective view of a microscope slide having an area of cells deposited thereon, after removal of the elongated hollow tube.

FIG. 4 shows the microscope slide 24 having a cell deposit 31 thereon, after removal of the tube 10.

Having described the structures of each of the components of the apparatus, a description of how to use the apparatus follows. FIGS. 1 and 2 show the interrelation between the components of the apparatus of the invention. A microscope slide 24 is placed onto the flat surface of the recessed area 29 of base plate 26. The elongated hollow tube 10 then is placed on the slide surface so that the O-ring 22 abuts the slide surface, and so that the outwardly-extending connector flange 16 fit into slots 28a, 28b of base plate 26. Once in this position, the tube 10 is forced in a downwardly manner to compress the O-ring 22 against the slide surface, and then the tube 10 is rotated so that the connector flanges 16 and guide flanges 18 are received and held in place by passage 30. The downward force exerted by the tube 10 on the microscope slide through O-ring 22 is sufficient to securely hold the slide in place in recessed area 29 during the depositing and staining of the cytological material on the slide surface.

The cytological material to be analyzed is received from the doctor's clinic in a sample vial. The cells may be taken directly from this sample vial and inserted into the chamber 14 of the apparatus of the invention, or may be processed further, for example, cell clumps may be disaggregated, the sample may be centrifuged over a density gradient, etc., prior to transfer to the apparatus of the invention.

When using the apparatus of the invention, the technician will place a predetermined amount of the sample cell suspension into the chamber 14. The cells can be allowed to settle onto the slide under natural gravitational force or centrifugal force, which slide preferably has been coated with a cationic material, such as Poly-L lysine. The ionic attraction between the negatively-charged cells and the positively-charged slide surface provide the adhesive force needed to keep the cells in place during subsequent processing. The O-ring 22 prevents any leakage of liquid at the interface of the slide surface and the bottom end of the tube 10. After settlement of the cells on to the slide, the supernatant is removed by aspiration which also includes removal of excess cells which have not adhered to the slide. The cells collected on the slide are then treated in a conventional manner.

The apparatus of the invention permits the cell collection to be stained using standard staining methods with the tube 10 still in place on the slide, thereby preventing the undesirable "floating" of cells from one sample slide to another sample slide. After staining, tube 10 is rotated in the direction reverse to that necessary to lock it to the base plate 22, and the tube 10 is removed leaving the microscope slide in the base plate 22. The slide then is ready for either manual or automated analysis of the cells prepared thereon.

The above-described apparatus is best suited for use on an automated cytological specimen analyzer system since the configuration of the base plate 26 makes it suitable for arrangement in a plurality. As such, it is an aspect of the invention to provide a plurality of the apparatuses of the invention, all of which are interconnected in a series, as part of an automated operation. Thus, the depositing of the cytological material and the subsequent staining can be done automatically on a large number of samples without the need for human intervention.

It is understood that other variations on the above-described invention can be made by one of skill in the art without departing from the scope of the invention, which scope is defined by the appended claims.

What is claimed is:

1. An apparatus for use in depositing and staining cytological material on a microscope slide, which comprises:
   a) an elongated hollow tube having a top end and a bottom end;
   b) a base member attached to the bottom end of the tube and projecting outwardly from said tube perpendicular to the longitudinal axis of the tube;
   c) at least one flange connected to the base member and outwardly-extending from the base member and perpendicular to the longitudinal axis of the tube; and
   d) a base plate which defines a recessed area configured to receive the microscope slide, the base plate further defining at least one slot, one slot for each respective flange and extending upwardly from the recessed area, each slot configured and dimensioned for receiving the flange, the base plate further defining a passage which extends from said slot for a releasably securing the respective flange when the tube is rotated.

2. The apparatus according to claim 1, wherein the flange has a terminal end and includes a guide flange positioned at the terminal end, which guide flange is disposed substantially perpendicular to the flange.

3. The apparatus according to claim 1, wherein the tube includes two diametrically opposed flanges extending from the base member.

4. An apparatus for use in depositing and staining cytological material on a microscope slide comprising:
 a) an elongated hollow tube having a top end and a bottom end;
 b) a disk-shaped base member attached to the bottom end of the tube and projecting outwardly from the tube perpendicular to the longitudinal axis of the tube;
 c) first and second flanges connected to the disk-shaped base and outwardly-extending from the base member perpendicular to the longitudinal axis of the tube, the flanges each having a terminal end;
 d) a first guide flange positioned at the terminal end of the first flange, and a second guide flange positioned at the terminal end of the second flange, which first and second guide flanges are disposed substantially perpendicular to the respective flanges; and
 e) a base plate which defines a recessed area configured to receive the microscope slide, the base plate further defining first and second slots extending outwardly from the recessed area, the first slot for receiving said first flange and the second slot for receiving the second flange, the base plate further defining first and second passages which extend from the first and second slots, respectively, along a plane substantially parallel to the recessed area, the first and second passages for receiving and releasably securing locking the first and second flanges, respectively, when the tube is rotated.

* * * * *